United States Patent [19]

Maxwell

[11] Patent Number: 5,048,525
[45] Date of Patent: * Sep. 17, 1991

[54] BLOOD PARAMETER MEASUREMENT SYSTEM WITH COMPLIANT ELEMENT

[75] Inventor: Thomas P. Maxwell, Santa Ana, Calif.

[73] Assignee: Minnesota Mining and Manufacturing Company, St. Paul, Minn.

[*] Notice: The portion of the term of this patent subsequent to Jun. 19, 2007 has been disclaimed.

[21] Appl. No.: 539,602

[22] Filed: Jun. 18, 1990

Related U.S. Application Data

[60] Continuation-in-part of Ser. No. 328,056, Mar. 23, 1989, Pat. No. 4,934,369, which is a division of Ser. No. 8,937, Jan. 30, 1987, Pat. No. 4,830,013.

[51] Int. Cl.$^5$ .................................................. A61B 5/00
[52] U.S. Cl. ..................................... 128/637; 128/692
[58] Field of Search ............... 128/637, 692, 632, 634, 128/635, 673

[56] References Cited

U.S. PATENT DOCUMENTS

| | | | |
|---|---|---|---|
| Re. 31,879 | 5/1985 | Lubbers et al. | 436/133 |
| 2,629,399 | 2/1953 | Kulick | 604/118 |
| 3,433,935 | 3/1969 | Sherman | 128/634 |
| 3,461,856 | 8/1969 | Polanyi | 128/633 |
| 3,498,286 | 3/1970 | Polanyi et al. | 128/673 |
| 3,512,517 | 5/1970 | Kadish et al. | 128/635 |
| 3,529,591 | 9/1970 | Schuette | 128/692 |
| 3,612,866 | 10/1971 | Stevens | 250/483.1 |
| 3,616,409 | 10/1971 | Tosteson | 204/195 |
| 3,658,053 | 4/1972 | Fergusson et al. | 128/632 |
| 3,674,013 | 4/1973 | Polanyl | 356/241 |
| 3,807,390 | 4/1974 | Ostrowski et al. | 356/41 |
| 3,814,081 | 6/1974 | Mori | 356/41 |
| 3,841,308 | 10/1974 | Tate | 604/249 |
| 3,866,599 | 2/1975 | Johnson | 128/348 |
| 3,878,830 | 4/1975 | Bicher | 128/632 |
| 3,893,448 | 7/1975 | Brantigan | 128/632 |
| 3,983,864 | 10/1976 | Sielaff et al. | 128/632 |
| 4,008,717 | 2/1977 | Kowarski | 128/632 |
| 4,016,864 | 4/1977 | Sielaff et al. | 128/632 |
| 4,050,450 | 9/1977 | Polanyi | 356/41 |
| 4,073,297 | 2/1978 | Kopp | 128/634 |
| 4,187,856 | 2/1980 | Hall et al. | 128/635 |
| 4,200,110 | 4/1980 | Peterson et al. | 128/634 |
| 4,201,222 | 5/1980 | Haase | 128/673 |
| 4,210,029 | 7/1980 | Porter | 128/634 |
| 4,265,249 | 5/1981 | Schindler et al. | 128/635 |
| 4,274,417 | 6/1981 | Delpy | 128/632 |
| 4,295,470 | 10/1981 | Shaw et al. | 128/634 |
| 4,311,137 | 1/1982 | Gerard | 604/28 |
| 4,322,164 | 3/1982 | Shaw et al. | 128/632 |
| 4,340,615 | 7/1982 | Goodwin et al. | 128/632 |
| 4,398,542 | 8/1983 | Cunningham et al. | 128/675 |
| 4,407,290 | 10/1983 | Wilber | 128/633 |

(List continued on next page.)

FOREIGN PATENT DOCUMENTS

| | | |
|---|---|---|
| 0276977 | 1/1988 | European Pat. Off. . |
| 2215984 | 10/1972 | Fed. Rep. of Germany ...... 128/634 |
| WO84/01109 | 9/1983 | PCT Int'l Appl. . |
| 1593270 | 11/1976 | United Kingdom ................ 128/632 |

OTHER PUBLICATIONS

IEEE Transactions on Biomedical Engineering, vol. BME-33, No. 2, "Optical Fluorescence and its Application to an Intravascular Blood Gas Monitoring System", pp. 117-132, IEE, New York, J. L. Gehrich et al., (Feb. 1986).

Primary Examiner—Francis Jaworski
Assistant Examiner—George Manuel
Attorney, Agent, or Firm—Gary L. Griswold; Walter N. Kirn; Dale E. Hulse

[57] ABSTRACT

An assembly for the measurement of a blood parameter comprising a catheter having a lumen extending therethrough and a sensor mounted in the lumen. A conduit couples the lumen to a source of anti-clotting solution, and a compliant element is coupled to the conduit to allow the volume of the introducing system to be expanded and contracted. The compliance of the compliant element can be adjusted to thereby adjust the compliance of the assembly.

13 Claims, 4 Drawing Sheets

FIG. 1

U.S. PATENT DOCUMENTS

| Patent No. | Date | Inventor | Class |
|---|---|---|---|
| 4,471,765 | 9/1984 | Strauss | 600/5 |
| 4,476,870 | 10/1984 | Peterson et al. | 128/634 |
| 4,476,877 | 10/1984 | Barker | 128/236 |
| 4,478,222 | 10/1984 | Koning et al. | 128/632 |
| 4,502,488 | 3/1985 | Degironimo et al. | 128/692 |
| 4,508,123 | 4/1985 | Wyatt et al. | 128/692 |
| 4,535,786 | 8/1985 | Kater | 128/760 |
| 4,543,961 | 10/1985 | Brown | 128/667 |
| 4,557,900 | 12/1985 | Heitzmann | 422/55 |
| 4,573,968 | 3/1986 | Parker | 604/67 |
| 4,585,007 | 3/1986 | Uchigaki et al. | 128/632 |
| 4,601,706 | 7/1986 | Aillon | 128/673 |
| 4,608,996 | 9/1986 | Brown | 128/760 |
| 4,640,820 | 2/1987 | Cooper | 422/68 |
| 4,651,741 | 3/1987 | Passafaro | 128/633 |
| 4,684,245 | 8/1987 | Goldring | 128/634 |
| 4,718,423 | 9/1986 | Willis et al. | 128/634 |
| 4,736,748 | 3/1988 | Nakamura et al. | 128/632 |
| 4,774,955 | 10/1988 | Jones | 128/632 |
| 4,785,814 | 11/1988 | Kane | 128/634 |
| 4,810,655 | 3/1989 | Khalil et al. | 128/633 |
| 4,830,013 | 5/1989 | Maxwell | 128/637 |
| 4,832,034 | 5/1989 | Pizziconi et al. | 128/632 |
| 4,934,369 | 6/1990 | Maxwell | 128/637 |
| 4,941,475 | 7/1990 | Williams et al. | 128/692 |
| 4,974,592 | 12/1990 | Branco | 128/635 |

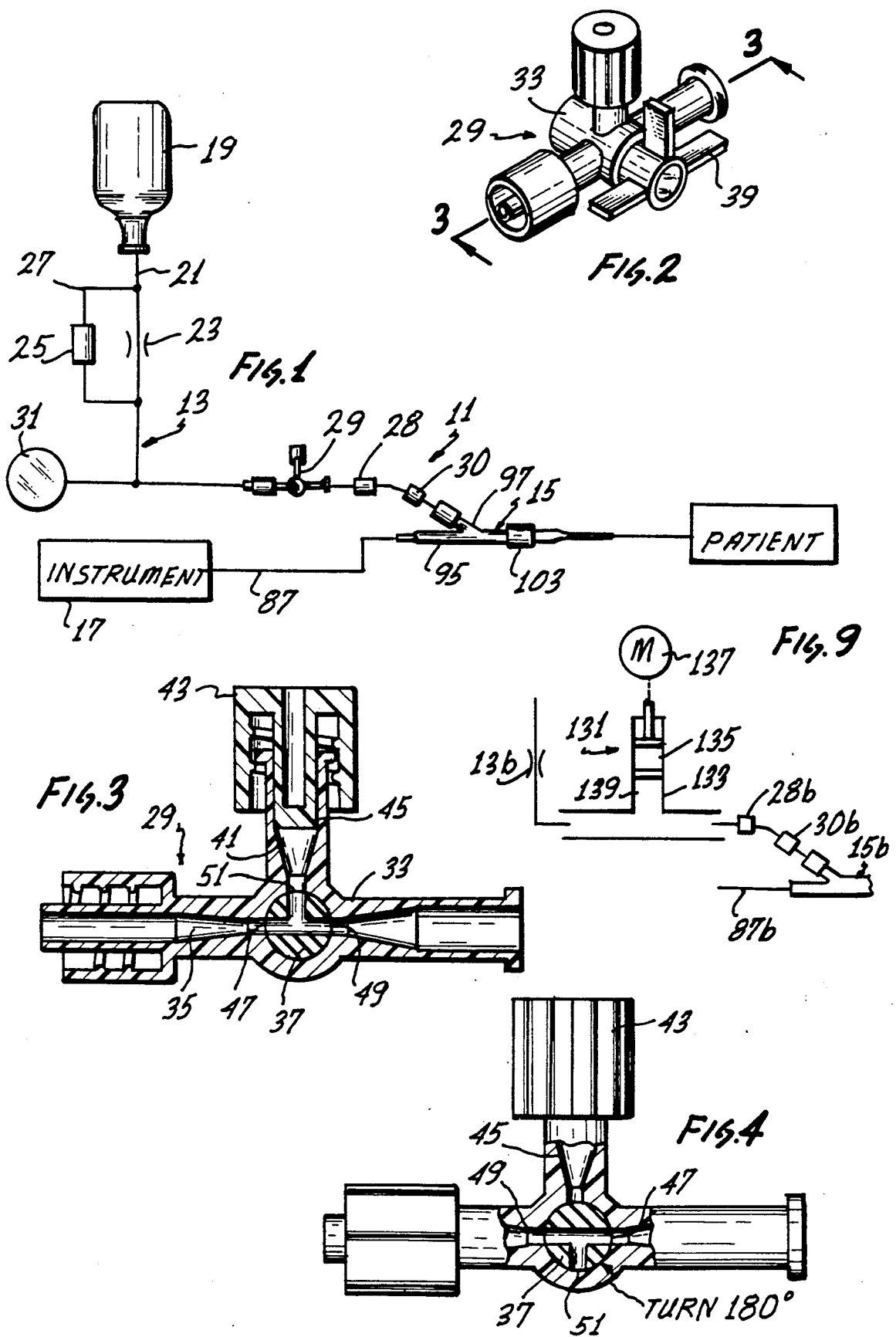

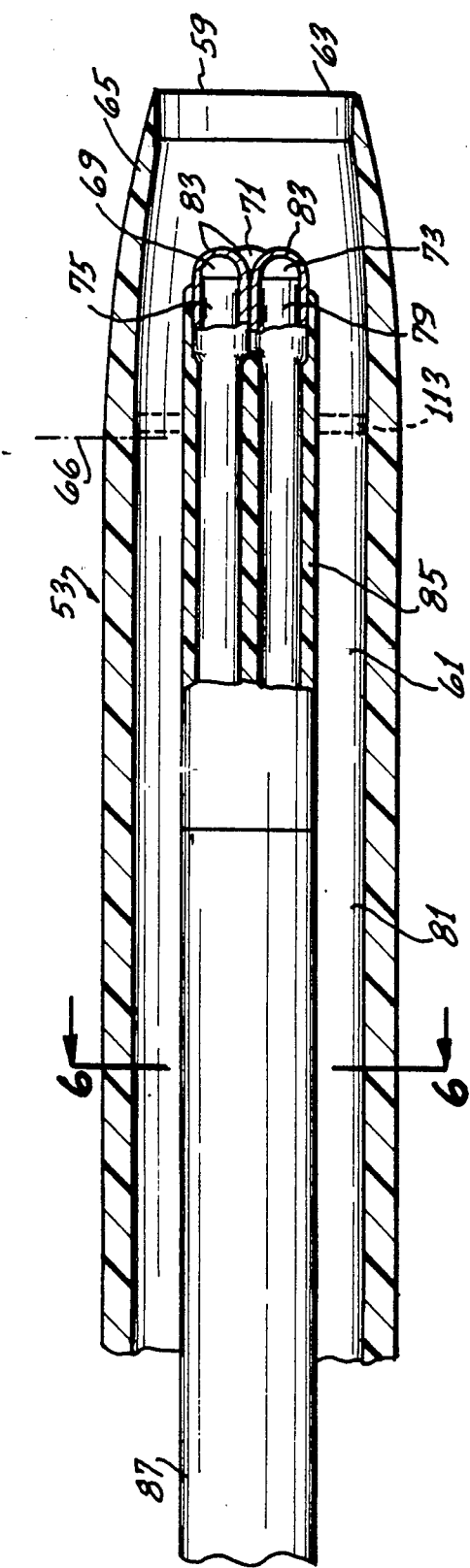
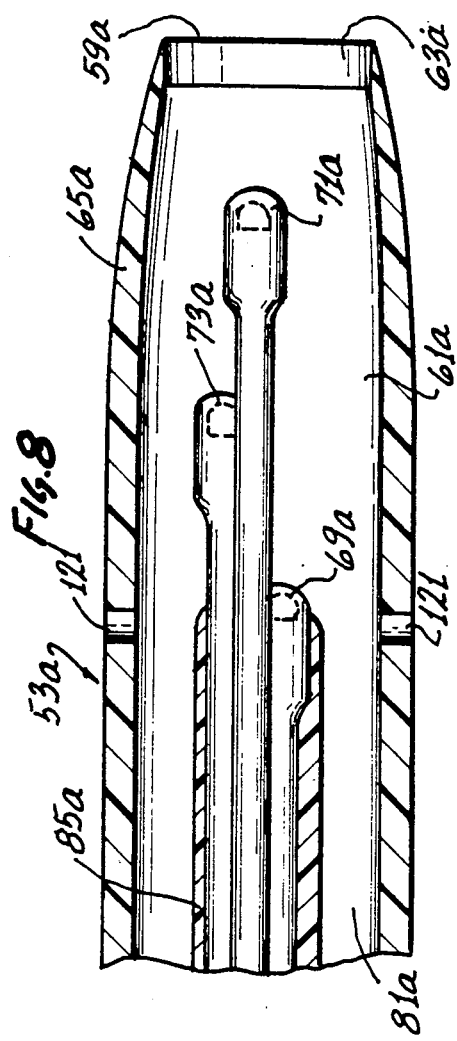
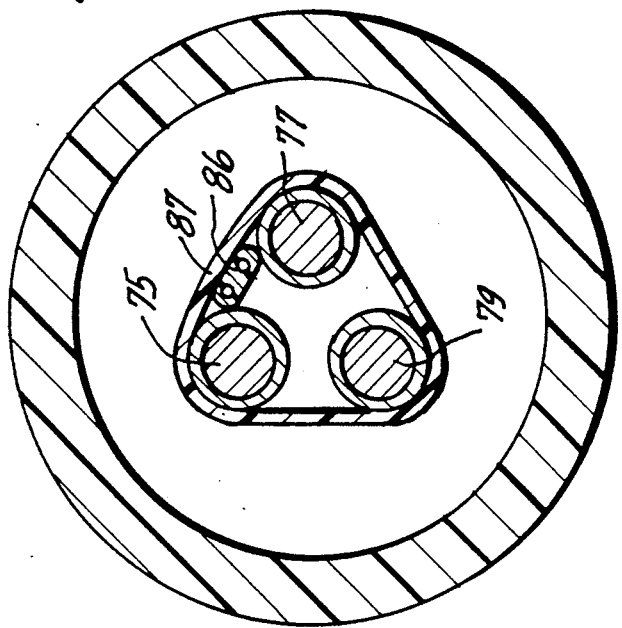

BLOOD PARAMETER MEASUREMENT SYSTEM WITH COMPLIANT ELEMENT

BACKGROUND OF THE INVENTION

This application is a continuation in part of application Ser. No. 328,056 filed on Mar. 23, 1989 now U.S. Pat. No. 4,934,369, which is a division of application Ser. No. 8937 filed Jan. 30, 1987, now U.S. Pat. No. 4,830,013.

It is often necessary or desirable to measure various parameters of blood, such as temperature and blood constituents, such as blood gases, pH, other electrolytes and glucose. This can be accomplished in real time using fluorescent sensors. For example, this can be accomplished in an extracorporeal blood loop as shown in Cooper application Ser. No. 546,493 filed on Oct. 28, 1983, and in vivo as disclosed in Lubbers et al Reissue U.S. Pat. No. 31,879. For in vivo sensing, a probe or catheter carrying an appropriate sensor is inserted into a blood vessel of the patient.

One of the most important gases that needs to be sensed is oxygen. One problem with in vivo oxygen sensing is that the readings obtained for the concentrations of oxygen tend to vary over an unacceptably wide range when compared with the results obtained using conventional laboratory techniques for measuring the concentration of oxygen. It has been found that this deviation is in many cases unacceptably large so that the reliability of the in vivo measuring system is called into question.

Grandparent U.S. Pat. No. 4,830,013 provides for effective in-vivo sensing of various blood parameters and provides a solution to phenomena known as the "wall effect" and the "clot effect." Although there are many facets to that invention, one feature involves keeping an in vivo sensor out of contact with the vessel wall. For this purpose, the sensor is carried by a probe, and the probe is adapted to be inserted through a catheter into the cardiovascular system.

The sensor can be mounted within the catheter in any desired way. A preferred system includes a probe-catheter assembly which comprises a probe including at least one sensor for sensing a parameter of blood and providing a signal in response thereto and elongated transmission means for transmitting the signal from the sensor proximally. The sensor is carried by a distal portion of the transmission means. The assembly also includes the catheter which has a lumen extending therethrough, a proximal end, a distal end and a distal opening at the distal end.

It is quite surprising that a sensor located within a catheter lumen could adequately sense the parameter of interest in blood. One reason for this is that it is necessary to introduce an anti-clotting solution, such as a heparinized saline solution, into the lumen from a solution-introducing system. The solution may be resident in the lumen, i.e., have no net flow into the vessel, but preferably it flows at a very low rate, such as 3 to 8 milliliters per hour, through the lumen and out through the distal opening of the catheter into the blood stream in the vessel. It is surprising that a sensor positioned in the lumen where there is an anti-clotting solution, particularly in the path of the distally flowing anti-clotting solution, would be able to adequately sense the parameters of interest in blood.

SUMMARY OF THE INVENTION

However, this invention recognizes that there is an interface between the blood and the anti-clotting solution. Theoretically, the interface could be a plane that simply divides the blood from the anti-clotting solution. However, in reality, the interface is a zone which has some axial length and which contains a mixture of the blood and the anti-clotting solution. Thus, the interface divides a zone of substantially all blood from a zone containing substantially all anti-clotting solution.

Because the anti-clotting solution may be supplied to the catheter such that there is a net flow of solution to the vessel, it would be expected that the interface would be entirely outside of, or at the distal end of, the catheter. However, by moving the interface back and forth in the lumen, the sensor can be exposed to blood for at least a portion of time that the interface is moving. This exposure must be sufficient to enable the sensor to provide an accurate signal related to the blood parameter of interest.

The movement of the interface back and forth in the lumen may move the interface over the sensor. However, the sensors, and in particular the oxygen sensor, can tolerate some exposure to the mixture of anti-clotting solution and blood in the interface without providing erroneous readings. For example, it has been found that a mixture consisting of 50 percent blood by volume and 50 percent anti-clotting solution by volume yields approximately the same oxygen concentration as the oxygen concentration in a medium consisting essentially of blood.

Movement of the interface to bathe the sensor within the lumen in blood can be brought about in different ways. For example, the interface may be moved by varying the delivery pressure and/or volume of the anti-clotting solution or providing the introducing system with a volume oscillator and allowing the volume oscillator to move the interface. The volume oscillator may, for example, take the form of a syringe which, in effect, expands and contracts the volume of the introducing system to move the blood back and forth in the lumen without creating a net or average flow in either direction.

The present invention is directed to another technique for moving the blood back and forth in the lumen. This technique, which also enables expansion and contraction of the volume of the introducing system, includes providing the introducing system with some compliance and allowing pressures generated by the patient's heartbeats to move the interface. Consequently, blood is forced to enter the distal opening of the catheter as the blood pressure rises with each beat of the heart. Thus, the interface is caused to flow back and forth in the lumen with the pulsating blood pressure. As a result, the sensor within the lumen is bathed by the back and forth or tidal movement of the blood and can adequately sense and measure the blood parameters of interest.

The compliance of the introducing system may be the natural compliance of the tubing and components of the system and/or a compliant element may be added to the system to provide the desired degree of elasticity. The compliant element can be of virtually any construction and may be, or include for example, a compressible fluid, such as air, a membrane, a bellows, etc. The compliance of the introducing system may be varied to obtain the results desired. For example, if the compliance of the introducing system is to be used to obtain, or to assist in obtaining, the tidal action, the introducing system and the catheter may have a combined total compliance sufficient to provide a volume exchange of at least 10 microliters with a system comprised of a 20-gauge catheter and 0.022 inch diameter probe.

The degree of compliance or elasticity required will vary from patient to patient. For example, a patient with high blood pressure will require a system with less compliance than a patient with low pressure. Selecting the proper degree of compliance is important because, if there is too little compliance, there is an increased risk that the sensor will not be adequately bathed in sufficient blood to get an accurate blood parameter reading. On the other hand, if there is too much compliance, the blood is withdrawn too far up into the system, and this increases the risk of clotting. Accordingly, it is important to select a degree of compliance which is within the maximum allowable or preferred compliance ranges.

This invention provides a system which includes at least first and second compliances and means for selecting the first compliance or the second compliance. This enables the physician or attendant to select the compliance most suited to a particular patient. For example, the selection may be between the natural compliance of the system and the compliance provided by utilizing a compliant element. In this event, the compliance selection is obtained by switching the compliant element into and out of communication with the lumen of the catheter. Thus, the choice is between the natural compliance and a compliance which equals the natural compliance plus an added compliance of the compliant element.

Alternatively or in addition thereto, a selection may be made between or among two or more compliances which are other than the natural compliance of the system. Such a system may include a compliant element and means for adjusting the compliance of the compliant element to thereby provide multiple different compliances which are greater than the natural compliance. Adjusting the added compliance can be very desirable, not only to more finely tune the compliance, but also to compensate for system-to system variations in the natural compliance.

As indicated above, the compliant element may take many different forms. In one preferred form, it includes an elastically movable membrane. Adjusting means is provided for limiting the maximum elastic movement of the membrane to thereby provide multiple compliances. Preferably, the limiting means is infinitely adjustable to provide an infinite number of compliances for the system. A preferred construction includes a housing having a passage in communication with the lumen of the catheter, with the membrane being mounted on the housing. In this event, the limiting means preferably includes a movable member mounted for movement on the housing to provide an adjustable stop for limiting movement of the membrane.

The compliance features of this invention are applicable to any system in which blood is withdrawn from a patient into a catheter or into an elongated passage of a system. In such a system, an anti-clotting solution or other fluid is introduced into the passage to provide the interface between the blood and the solution. This enables the user to select one of the compliances, and the interface moves back and forth in the passage, with the system having the selected compliance. The moving of the interface is the result of, or includes, allowing the patient's heartbeats to move the interface against the selected compliance. This movement of the interface enables sensing a parameter of the blood in the passage.

Broadly stated, an assembly constructed in accordance with this invention may include first means for withdrawing blood from a patient into the first means and for introducing a fluid, such as an anti-clotting solution, to the blood to provide a blood-fluid interface in the first means. The first means includes a catheter adapted to be received in a patient's cardiovascular system and having a lumen for receiving blood from the patient's cardiovascular system. The first means also includes means for introducing a fluid to the lumen whereby there is a blood-fluid interface in the first means. A sensor is provided in communication with the lumen, and the first means is compliant so that the patient's heartbeats tend to move the interface. The first means also has a first compliance and a second compliance and means for selecting the first compliance or the second compliance, with such compliances being different. The interface between the blood and fluid may be in the lumen of the catheter or elsewhere in the first means depending upon how far up into the system it is desired to withdraw blood.

It may be necessary or desirable to take the patient's blood pressure through the lumen of the catheter while the blood parameters are being sensed. The added compliance of the introducing system may be sufficient to undesirably alter the blood pressure readings taken through the lumen of the catheter. Accordingly, the present invention provides, as an option, for selectively nullifying the ability of the compliant element to allow expansion and contraction of the volume of the introducing system. For example, the nullifying means may control expansion or adjustably limit movement of a membrane or bellows or it may selectively switch the compliant element into, and out of, communication with the lumen of the catheter. In this latter event, the compliant element would normally be in communication with the lumen to provide, or assist in providing, the desirable tidal action for sensing of the blood parameters of interest. However, just prior to taking a blood pressure reading, the action of the compliant element can be switched out of the introducing system so that it cannot affect the blood pressure reading taken through the lumen of the catheter. The switching means may take any form that will accomplish this function and may be, for example, a valve.

The invention, together with additional features and advantages thereof, may best be understood by reference to the following description taken in connection with the accompanying illustrative drawing.

BRIEF DESCRIPTION OF THE DRAWING

FIG. 1 is a schematic view of an assembly for the in vivo measurement of blood parameters of interest.

FIG. 2 is a perspective view of one form of valve usable in the assembly of FIG. 1.

FIG. 3 is an axial sectional view through the valve with the compliant element being in communication with the conduit leading to the lumen of the catheter.

FIG. 4 is an elevational view partially in section and similar to FIG. 3 with the compliant element being out of communication with the conduit.

FIG. 5 is an enlarged fragmentary sectional view of the distal region of one form of probe and catheter usable in the assembly of FIG. 1.

FIG. 6 is an enlarged sectional view taken generally along line 6—6 of FIG. 5.

FIG. 8 is a sectional view similar to FIG. 5 showing an alternate construction of the distal region of the probe.

FIG. 9 is a schematic view similar to FIG. 1 showing another assembly for the in vivo measurement of blood parameters of interest.

DESCRIPTION OF THE PREFERRED EMBODIMENT

Figure 7:
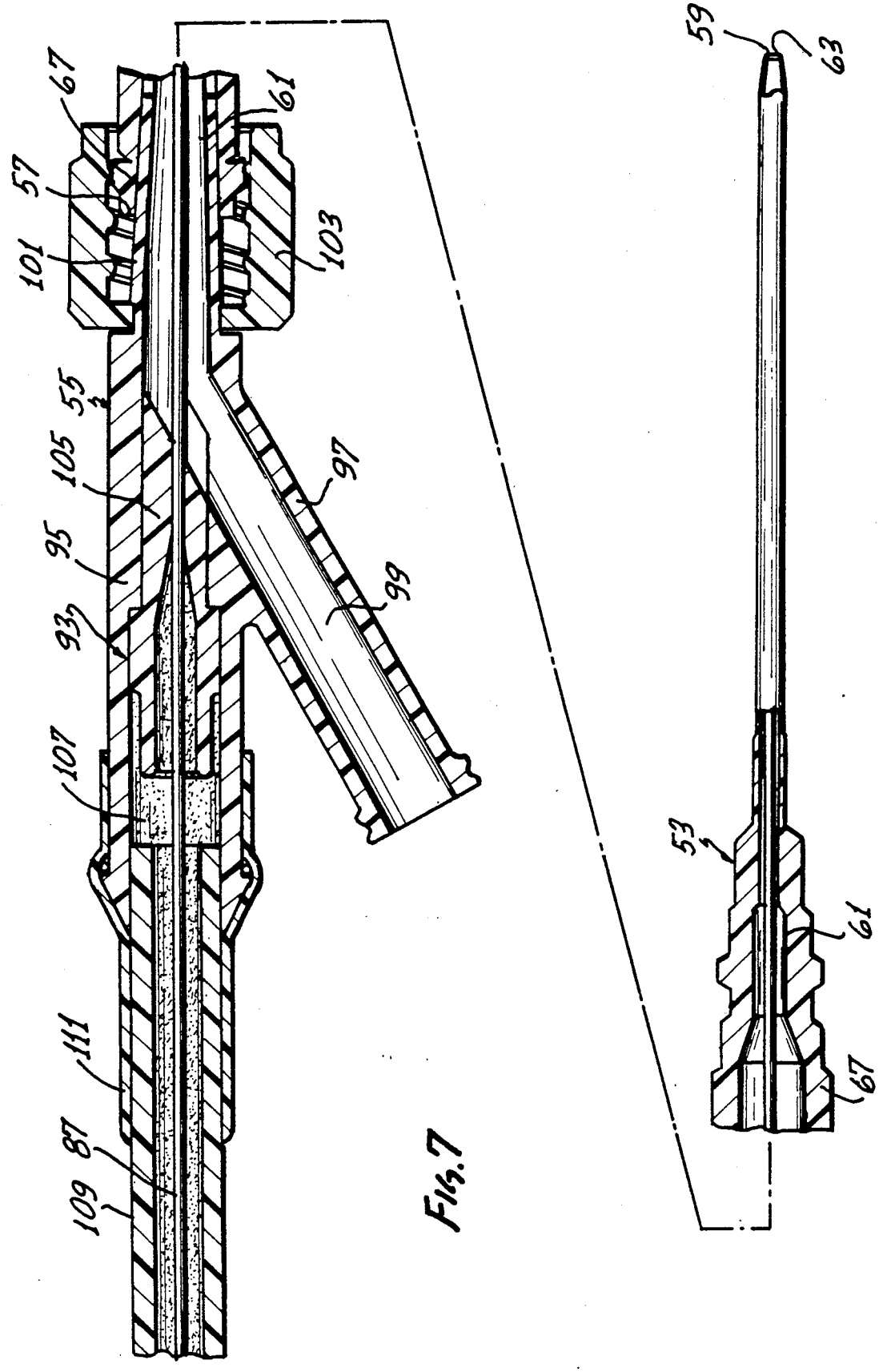
FIG. 7 is a longitudinal sectional view through the probe-catheter assembly.

FIG. 1 shows an assembly 11 for the in vivo measurement of various blood parameters, and particularly the pH value and the concentrations of oxygen and carbon dioxide. Although the assembly 11 can be of different constructions, in this embodiment it includes a solution introducing system 13 and a probe-catheter assembly 15. The assembly 11 may also include an instrument 17 for providing a readout of the blood parameters of interest.

Generally, the solution introducing system 13 introduces an appropriate anti-clotting solution, such as a heparinized saline solution, through the probe-catheter assembly 15 to the patient to keep the line leading to the patient patent. Although this can be accomplished in different ways, in the embodiment shown schematically in FIG. 1, the system 13 includes a pressurized source 19 of heparinized saline solution, a conduit 21 leading from the source to the probe-catheter assembly 15, a flow restrictor 23 to reduce the rate of flow through the conduit 21 to the desired drop rate, a flush valve 25 in a bypass 27 around the restrictor 23, a stop cock 28, a four-way valve 29, a blood withdrawal site 30 and a pressure transducer 31. All of the components of the system 13 may be conventional, and the system 13 may include other components, if desired. In the illustrated embodiment, solution from the pressurized source 19 flows through the restrictor 23 at a relatively slow rate, such as 5 ml/hour. The solution flows through the valve 29 and the probe-catheter assembly 15 to the patient. If a more rapid flow rate from the source 19 is desired, as for example during priming, the flush valve 25 can be manually opened to provide a relatively high-rate flow path around the restrictor 23 in a conventional manner.

The four-way valve 29 may also be of conventional construction. As shown in FIG. 3, the valve 29 includes a valve body 33 having a passage 35 extending therethrough and forming a portion of the conduit 21, a rotatable valve element 37 in the passage 35 and a handle 39 (FIG. 2) for manually rotating the valve element 37. The valve body 33 has a leg 41, and a closure cap 43 is attached to the leg 41 to define, along with the leg, a chamber 45 in which a compliant element in the form of air is located. The valve element 37 has ports 47 and 49 for communicating with the conduit 21, and a port 51 which can communicate with the chamber 45 as shown in FIG. 3 or which can be sealed and out of communication with the conduit 21 and the chamber 45 as shown in FIG. 4. In this manner, the compliant element can be switched into, or out of, the system 13.

The pressure transducer 31 communicates with the conduit 21 and can measure the pressure therein. Accordingly, with the probe-catheter assembly 15 inserted into the vascular system of a patient, the pressure transducer 31 can provide blood pressure readings. By rotating the valve element 37 to the position of FIG. 4, the compliance of the air within the chamber 45 cannot affect the blood pressure readings provided by the transducer 31. The blood withdrawal site 30 is used for taking blood samples from the patient through the probe-catheter assembly 15. Preferably for this kind of compliant element, the stop cock 28 is located between the valve 29 and the site 30 so that, by closing the stop cock 28, the air in the chamber 45 cannot be withdrawn during a blood withdrawal procedure.

The probe-catheter assembly 15 includes a catheter 53 and a probe 55 (FIG. 7). The catheter 53 may be a conventional arterial catheter. As such, the catheter 53 may include a proximal end 57, a distal end 59, a lumen 61 extending axially, completely through the catheter and opening at a distal opening 63 at the distal end. The catheter 53 has a standard lead-in taper, i.e., a tapered zone 65, which extends from a reference plane 66 along the outer periphery of the catheter 53 to the distal end 59. The diameter of the lumen 61 also decreases distally throughout the tapered zone 65 as shown in FIG. 5. The tapered zone 65 may extend about 0.090 inch proximally of the distal end 59. The catheter 53 has an externally threaded coupling 67 at its proximal end.

The probe 55 may be of various different constructions, and in the embodiment illustrated, includes an oxygen sensor 69, a carbon dioxide sensor 71 and a pH sensor 73, with each of the sensors affixed to the distal ends of single optical fibers 75, 77, and 79, respectively, (FIG. 6). In this embodiment, the sensors 69, 71 and 73 are fluorescent optical sensors, and they respond to the concentration of oxygen, the concentration of carbon dioxide and the pH value, respectively, to provide continuous optical signals indicative of the condition sensed. The optical fibers 75, 77 and 79 serve as transmission means for transmitting the signals from the associated sensors proximally. The probe 55 is of very small cross-sectional area so that it fits within the lumen 61 with an ample radial clearance 81 as shown in FIG. 5.

The particular design of the probe 55 forms no part of this invention because this invention is applicable to probes of various different constructions. Briefly, however, the sensors 69, 71 and 73 are attached to the distal ends of the associated optical fibers 75, 77 and 79 in any suitable manner, and each of the sensors and the associated fiber is separately encased in an inner overcoat 83 which, among other things, may assist in retaining the sensor on the end of the associated fiber. The overcoat 83 is, of course, permeable to the relevant blood parameters so that such parameter, or one related to it, can be sensed by the sensors. An outer overcoat 85 covers the inner overcoats 83 and a length of the fibers just proximally of the overcoats 83. Proximally of the overcoat 85, the optical fibers 75, 77 and 79 and a temperature-sensitive element, such as a thermocouple 86 (FIG. 6), are suitably encased within an appropriate sheath 87.

The probe 55 includes a "Y" fitting 93 at its proximal end as shown in FIG. 7. The optical fibers 75, 77 and 79 extend within the sheath 87 completely through one leg 95 of the "Y" fitting 93 to the instrument 17 as shown in FIG. 1. Another leg 97 of the fitting 93 has a passage 99 which communicates with the lumen 61, and more particularly, with the clearance 81 around the probe 55. The leg 97 is coupled to the conduit 21 of the system 13 as shown in FIG. 1. A third leg 101 of the "Y" fitting 93 carries a rotatable internally threaded coupling 103 for attaching the "Y" fitting of the probe 55 to the proximal end of the catheter 53 outside the cardiovascular system of the patient.

Although the details of the fitting 93 form no part of this invention, the sheath 87 may be guided in the leg 95 by a sleeve 105 and retained in position by potting 107. The sheath 87 extends within a flexible tube 109 suitably attached to the leg 95, and shrink tubing 111 is provided over the adjacent end portions of the fitting and the tube for strain relief.

With the proximal end of the catheter 53 coupled to the probe 55 by the coupling 103, the probe 55 is within the lumen 61, and the sensors 69, 71 and 73 are within the lumen adjacent the distal opening 63 as shown in FIG. 5. Accordingly, with the catheter within the cardiovascular system of the patient, such as in a radial artery, the catheter 53 keeps the sensors from contacting the wall of the artery to thereby reduce or eliminate the wall effect and the clot effect on the signals provided by the sensors.

In use of the assembly 11, the catheter 53 is first inserted into the radial artery using conventional techniques. Next, the probe 55 is inserted into the lumen 61 and attached to the proximal end of the catheter 53 with the coupling 103. This properly positions the sensors 69, 71 and 73 within the lumen 61 to within 0.125 inch of the distal end 59. In priming the solution introducing system 13 prior to insertion of the catheter into the artery, a small quantity of air is trapped in the chamber 45. This can be accomplished, for example, with the valve element 37 in the position of FIG. 4, by filling the conduit 21 with solution from the source 19 with the closure cap 43 removed from the valve 29, and without allowing the solution to flow into the leg 41. The closure cap 43 is then affixed to the leg 41 to trap the air in the chamber 45, and then the rotatable valve element 37 is turned to the position shown in FIG. 3. The conduit 21 can then be connected to the probe 55.

When in use, the solution from the source 19 completely fills the lumen 61 around the probe 55. The solution is provided under a pressure such that there is a slow flow of solution from the lumen 61 into the patient's artery. This introduction of the solution through the lumen and into the artery results in an interface 113 adjacent the distal opening 63 which has some axial length and which includes both blood and the solution from the source 19. The interface 113 is a partition between essentially all blood distally of the interface and essentially all anti-clotting solution proximally of the interface. The interface washes axially back and forth in a tidal action as a result of the rising and falling of the patient's blood pressure with each heartbeat. If the solution introducing system 13 were perfectly rigid, it would not be possible for the blood to force the solution proximally within the lumen 61 because the solution is essentially incompressible. However, the conduit 21 is typically in the form of flexible plastic tubing, which has some elasticity or compliance to allow some of this tidal action to occur. In addition, the illustrated embodiment of the invention provides a compliant element in the form of air within the chamber 45 which adds additional elasticity or compliance to the system 13. Consequently, the interface can flow back and forth to bathe the sensors 69, 71 and 73 in blood.

With this embodiment of the invention, the back and forth travel of the interface 113 is a function of the magnitude of the patient's blood pressure, the compliance of the solution-introducing system 13 and the delivery pressure of the anti-clotting solution. However, assuming that there is some net flow of the anti-clotting solution out of the distal opening 63, it would be necessary for at least the distal region of the interface 113 to travel distally as far as the distal opening, unless it is possible for some of the solution to migrate through the blood and through the distal opening. Because the flow rate of anti-clotting solution into the bloodstream is extremely low, the precise manner in which the solution enters the patient's bloodstream and the exact extent of travel of the interface 113 is not known. However, utilizing the tidal action of the interface, it is possible to bathe the sensors 69, 71 and 73 in blood sufficiently so that accurate readings are obtained, and it is believed that the sensors are in essentially all blood for a majority of the time.

FIG. 8 shows another embodiment of this invention which is identical to the embodiment of FIGS. 1–7 in all respects not shown or described herein. Portions of the embodiment of FIG. 8 corresponding to portions of the embodiment of FIGS. 1–7 are designated by corresponding reference numerals followed by the letter "a."

The primary differences between the embodiment of FIG. 8 and FIGS. 1–7 is that the sensors 69a, 71a, 73a are at different longitudinal positions within the lumen 61a, the sensors 71a and 73a project farther from the overcoat 85a, and there are a plurality of radial apertures 121 in the catheter 53a leading from the lumen 61a adjacent the distal opening 63a of the catheter. In this embodiment, each of the three sensors terminates at a different axial position within the lumen 61a, and with this construction, the total cross-sectional area of the probe 55a reduces in step-wise fashion from the distal end of the sensor 71a proximally. Consequently, not all of the sensors are in the tapered zone 65a, and a larger cross-sectional area of the tapered zone remains open for pressure sensing via the pressure transducer 31 shown in FIG. 1.

In the construction of FIG. 8, preferably the carbon dioxide sensor 71a is the most distal sensor, and the oxygen sensor 69a is the most proximal. The reason for this is that carbon dioxide is the most sensitive to being even partially out of the blood, and the oxygen sensor can provide acceptable oxygen readings even in a fifty-fifty mixture of the blood and the anti-clotting solution. The sensitivity of the pH sensor 73a is intermediate the sensitivity of the carbon dioxide sensor 71a and the oxygen sensor 73a and so is preferably located intermediate these sensors.

The radial apertures 121 are preferably located proximally of the sensor 73a for the purpose of allowing blood and solution from the lumen 61a to flow out of the apertures. One or more of these apertures may be provided, and in the embodiment of FIG. 8, two of the apertures are shown. Of course, the apertures 121 may be distributed in axially spaced relationship, as well as circumferentially spaced relationship, along the catheter 53a. The apertures 121 may also be used in the embodiment of FIGS. 1–7, if desired.

FIG. 9 shows another embodiment of this invention which is identical to the embodiment of FIGS. 1–7 in all respects not shown or described herein. Portions of the embodiment of FIG. 9 corresponding to portions of the embodiment of FIGS. 1–7 are designated by corresponding reference numerals followed by the letter "b."

The only difference between the embodiment of FIG. 9 and FIGS. 1–7 is that the valve 29 has been replaced with a volume oscillator 131. Although the volume oscillator 131 can take different forms, including that of a conventional syringe, in this embodiment, it is illustrated schematically as including a cylinder 133 in communication with the conduit 21, a piston 135 slidable in the cylinder and a motor 137 for reciprocating the piston 135 through an appropriate reciprocating drive (not shown), such as a cam shaft. When the piston 135 is moved upwardly as viewed in FIG. 9, a chamber 139 below the piston is enlarged to expand the volume of the introducing system 13b. Conversely, when the piston 135 moves downwardly, the volume of the chamber 139 is decreased to thereby contract the volume of the introducing system. Of course, expansion of the introducing system 13b pulls the interface 113 (FIG. 5) proximally. Contraction of the introducing system moves the interface distally, with the amount of such movement being a function of the degree to which the volume oscillator 131 expands and contracts the volume of the introducing system.

The motor 137 can be operated continuously, intermittently or upon demand to create the tidal action. There is no net or average flow of fluid in either direction as a result of reciprocation of the piston 135. Of course, the volume oscillator 131 can also be used with the embodiment of FIG. 8.

Figure 10:
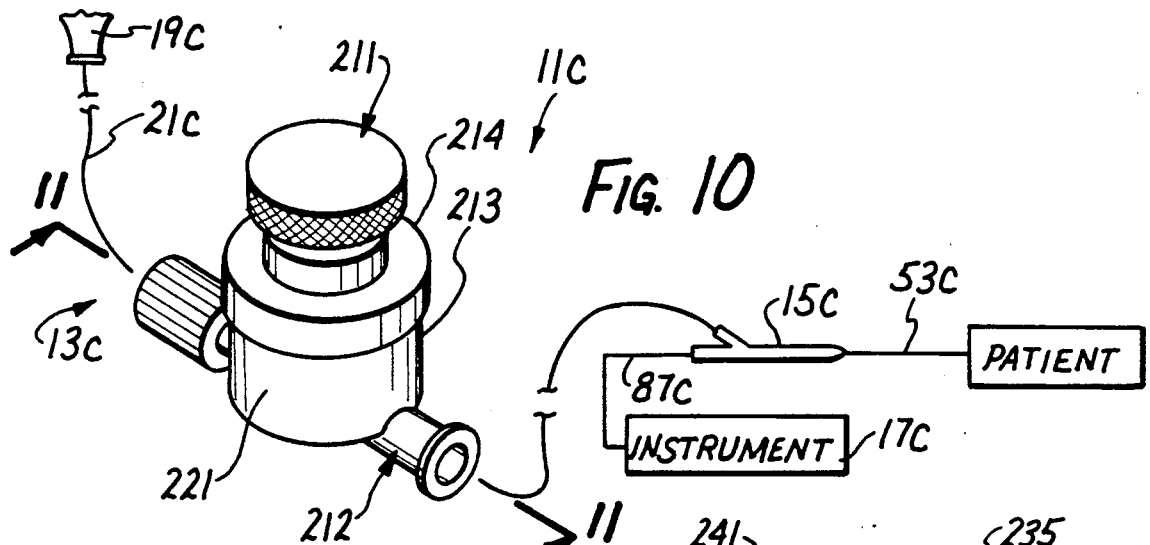
FIG. 10 is a schematic view of an assembly for the measurement of blood parameters of interest which incorporates another form of compliant element.

FIG. 10 shows an assembly 11c which is identical to the assembly 11 of FIG. 1 in all respects not shown or described herein. Portions of the assembly 11c corresponding to portions of the assembly 11 are designated by corresponding reference numerals followed by the letter "c." Although some of the components shown in FIG. 1 for the assembly 11 are not duplicated in FIG. 10 for the assembly 11c, the assembly 11c may nevertheless include all of such components.

The assembly 11c, like the assembly 11, includes first means for withdrawing blood from a patient into the first means and for introducing a fluid to the blood to provide a blood-fluid interface in the first means. Such first means includes a catheter 53c which, like the catheter 53, is adapted to be received in a patient's cardiovascular system and has a lumen for receiving blood from the patient's cardiovascular system. Such first means also includes an introducing system or means 13c for introducing a fluid, such as an anticlotting solution, to the lumen so that there is a blood-fluid interface in the first means. A sensor may be provided in the catheter 53c as described above in connection with the assembly 11. However, with this embodiment of the invention, the sensor may be provided in the catheter 53c and/or in the conduit 21c at any location where it will have adequate contact with the blood to provide an accurate reading of the blood parameter of interest. Thus, it is only necessary that the sensor be in communication with the lumen.

Turning now to a primary difference between the assemblies 11 and 11c in the assembly 11c, the valve 29 with the associated compliant element is replaced in favor of a compliance component 211.

The compliance component 211 includes a housing 212. Although the housing 212 can be of various different constructions, in the embodiment illustrated, it comprises housing sections 213 and 214. The housing section 213 has a passage 215 extending therethrough and in communication with the lumen of the catheter 53c. Conventional coupling components 217 and 219 are provided on the housing section 213 adjacent opposite ends of the passage 215 for releasably coupling the compliance component 211 into the conduit 21c in the same location as the four-way valve 29 of FIG. 1. The housing has an internally threaded boss 221.

A compliant element in the form of an elastic membrane 225 is mounted on the housing. Although various constructions are possible, the membrane 225 includes an annular bead 227 which is received in an annular gap defined by the boss 221 and an annular ridge 229 within, and coaxial with, the boss. The membrane 225 extends across a region of the housing section 213 and defines with such region of the housing a flow-through chamber 231.

Figure 11:
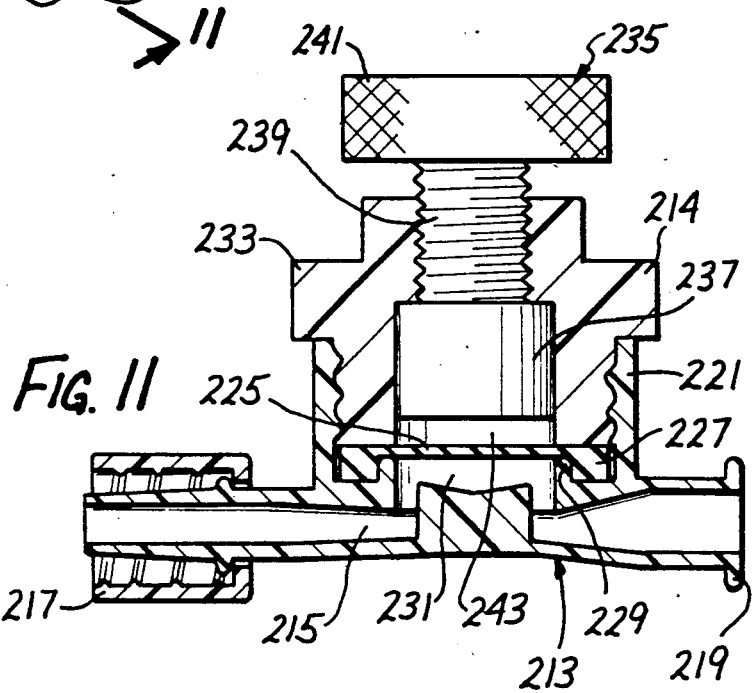
FIGS. 11 and 12 are sectional views taken generally along line 11—11 of FIG. 10 and illustrating one manner in which the compliance of the assembly can be adjusted.
Figure 12:
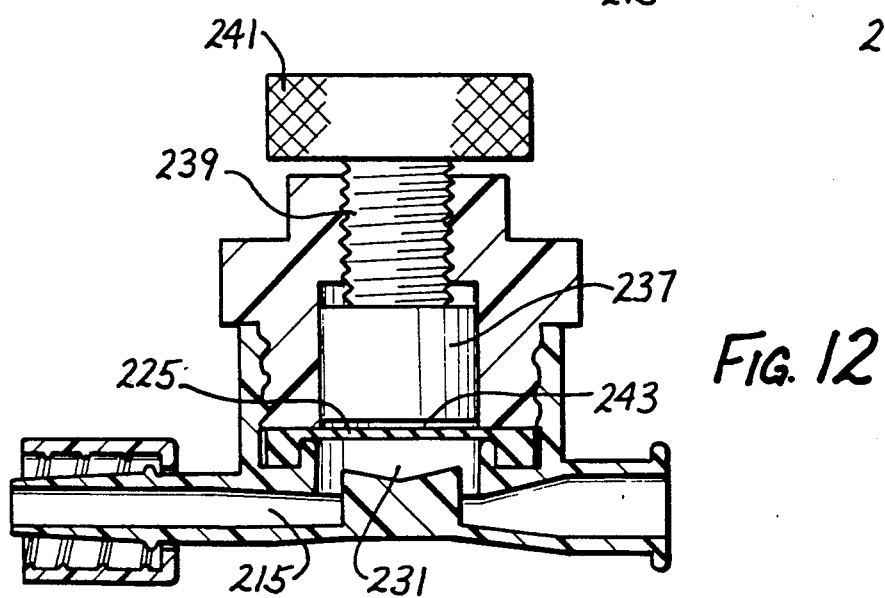

The housing section 214 includes a main body 233 and an adjustable stop 235. The main body 233 has external threads which are received within, and used to threadedly attach the main body to, the internal threads of the boss 221 as shown in FIGS. 11 and 12. When affixed in this position, the main body 233 engages the bead 227 of the membrane 225 to thereby mount the membrane in the housing.

The adjustable stop 235 includes an abutment 237, a threaded shaft 239 and an adjusting knob 241. The shaft 239 is threadedly received in a threaded bore of the main body 233. Accordingly, by manually turning the knob 241, the position of the abutment 237 can be adjusted.

FIGS. 11 and 12 show the membrane 225 in the relaxed or unpressurized condition. As shown in FIG. 11, there is a space or gap 243 between the membrane 225 and the abutment 237. This gap defines the maximum extent to which the membrane 225 can elastically expand or move in response to fluid pressure in the passage 215. FIG. 11 shows the maximum length of the gap 243 to thereby provide a relatively high degree of compliance to the system. The gap 243 can be reduced as shown, for example, in FIG. 12 by turning of the knob 241 in a direction to move the abutment 237 downwardly as viewed in FIG. 12. As the gap 243 is reduced, the allowable length that the membrane 225 can expand is correspondingly reduced to thereby reduce the compliance. Because of the threaded adjustment provided by the threaded shaft 239, the gap 243 is infinitely adjustable from a maximum all the way down to "0", in which event, the compliance of the membrane 225 is effectively removed from, or switched out of, the assembly 11c. When the compliance of the membrane 225 is effectively taken out of the assembly 11c, the assembly 11c is left with only its natural compliance which results from the inherent ability of the components and, in particular the conduit 21c, to expand under internal pressure.

The chamber 231 is sealed by the annular bead 227. However, the gap 243 is not sealed, and so upward movement of the membrane 225 does not compress air in the gap 243.

The operation of the assembly 11c is very similar to the operation of the assembly 11. Thus, blood is withdrawn from the patient by allowing it to flow under the influence of the patient's blood pressure into the lumen of the catheter 53c and, if desired, into the conduit 21c. An anticlotting solution is introduced into the conduit 21c from the source 19c, and the conduit conducts the solution to the catheter 53c to provide an interface between the blood and the solution. The interface is moved back and forth as a result of the patient's heartbeats, and the parameter of interest is sensed by the sensor as described above.

With the assembly 11, it is possible to select between two levels of compliance, i.e., the natural compliance of the system or a compliance which equals the natural compliance of the system plus the compliance of the air within the chamber 45. With the assembly 11, compliance selection is the result of operation of the four-way valve to either switch the compliant element into or out of the system.

With the assembly 11c, it is possible to not only switch the compliance of the membrane 225 into and out of the system, but also to adjust the compliance to be added by the membrane 225. This is accomplished as described above by turning of the knob 241 to adjust the gap 243.

Various techniques can be used to determine how much compliance should be provided for a particular system and patient. For example, the process may begin with the knob 241 turned to provide the minimum gap 243 and hence the minimum compliance. The gap 243 is gradually increased in small increments while the values of the blood parameters of interest are monitored at the instrument 17. When the values of the parameters of interest stabilize, this can be taken as the minimum compliance needed to achieve a correct reading. Increasing the compliance beyond this minimum amount should have little or no effect on the values of the parameters of interest, but if the compliance is much too great, the likelihood of clotting may increase. Of course, it is always possible to compare the values obtained at the instrument 17c with values obtained from a laboratory blood sample of the same patient and to use this information in establishing the degree of compliance that is to be used.

Although an exemplary embodiment of the invention has been shown and described, many changes, modifications and substitutions may be made by one having ordinary skill in the art without necessarily departing from the spirit and scope of this invention.

I claim:

1. An assembly for the measurement of a blood parameter comprising:
   first means for withdrawing blood from a patient into the first means;
   said first means comprising a catheter adapted to be received in a patient's cardiovascular system and having a lumen for receiving blood from the patient's cardiovascular system;
   said first means further comprising means for introducing a fluid into the lumen so as to form a blood-fluid interface in the first means;
   said first means being compliant whereby the patient's heartbeats tend to move the interface;
   said first means having a first compliance and a second compliance and comprising means for selecting the first compliance or the second compliance, said first and second compliances being different; and
   a sensor in communication with the lumen.

2. An assembly as defined in claim 1 wherein the introducing means has a natural compliance which provides the first compliance and the first means includes a compliant element for use in providing the second compliance, said second compliance being greater than the first compliance.

3. An assembly as defined in claim 2 including means for selectively switching the compliant element into and out of communication with the lumen of the catheter.

4. An assembly as defined in claim 1 wherein the first means has a compliant element and means for adjusting the compliance of said compliant element to thereby provide said first and second compliances.

5. An assembly as defined in claim 4 wherein the compliant element includes an elastic membrane and said adjusting means includes means for limiting maximum elastic movement of the membrane to thereby provide said first and second compliances.

6. An assembly as defined in claim 5 wherein the limiting means is infinitely adjustable to provide an infinite number of compliances for the introducing means.

7. An assembly as defined in claim 5 comprising a housing having a passage in communication with the lumen, said membrane being mounted on said housing and said limiting means including a movable member mounted for movement on the housing to provide an adjustable stop for limiting movement of the membrane.

8. An assembly for the in vivo measurement of a blood parameter comprising:
   a catheter comprising a lumen extending therethrough, a proximal end, a distal end and a distal opening at the distal end, said catheter being adapted to be received in a patient's cardiovascular system;
   a sensor for sensing the blood parameter and providing a signal in response thereto;
   means for mounting the sensor on the catheter with the sensor being within the lumen;
   a conduit for coupling the lumen to a source of fluid whereby the fluid can be supplied to the lumen;
   a compliant element coupled to said conduit to allow the volume of the assembly to be expanded and contracted;
   said compliant element including a membrane; and
   means for adjustably limiting movement of the membrane to adjust the compliance of the compliant element.

9. An assembly for the measurement of a blood parameter comprising:
   first means for withdrawing blood from a patient into the first means;
   said first means comprising a catheter adapted to be received in a patient's cardiovascular system and having a lumen for receiving blood from the patient's cardiovascular system;
   said first means further comprising means for introducing a fluid into the lumen so as to form a blood-fluid interface in the first means;
   said first means having a natural compliance whereby the patient's heartbeats tend to move the interface;
   said first means further comprising compliance means for providing the introducing means with a plurality of different compliances other than said natural compliance; and
   a sensor in communication with the lumen.

10. An assembly as defined in claim 9 wherein the introducing means includes a conduit communicable with the lumen of the catheter and the compliance means includes an elastic membrane and means for adjustably limiting movement of the membrane to provide said plurality of different compliances.

11. A method of sensing a parameter of blood comprising:

withdrawing blood from a patient into an elongated passage of a system having a plurality of different compliances;

introducing an anti-clotting solution into the passage to provide an interface between the blood and the solution;

selecting one of said compliances;

moving the interface back and forth in the passage with the system having said one compliance, said step of moving including allowing the patient's heartbeats to move the interface; and sensing a parameter of the blood in the passage.

12. A method as defined in claim 11 wherein said different compliances include a natural compliance of the system, wherein there is a compliant element in said system for use in providing a second of said compliances, and wherein said step of selecting includes selecting said natural compliance or said second compliance.

13. A method as defined in claim 11 wherein said different compliances include a natural compliance of the system, wherein there is a compliant element in said system for use in providing a plurality of other different compliances, and wherein said step of selecting includes using said compliant element to provide one of said other compliances.

* * * * *